(12) United States Patent
Fortin et al.

(10) Patent No.: US 8,814,800 B2
(45) Date of Patent: Aug. 26, 2014

(54) APPARATUS AND METHOD FOR ENHANCING AND ANALYZING SIGNALS FROM A CONTINUOUS NON-INVASIVE BLOOD PRESSURE DEVICE

(75) Inventors: Jürgen Fortin, Graz (AT); Rupert Grüllenberger, Graz (AT)

(73) Assignee: CNSystems Medizintechnik AG, Graz (AT)

( * ) Notice: Subject to any disclaimer, the term of this patent is extended or adjusted under 35 U.S.C. 154(b) by 873 days.

(21) Appl. No.: 12/915,496

(22) Filed: Oct. 29, 2010

(65) Prior Publication Data
US 2011/0105918 A1 May 5, 2011

Related U.S. Application Data

(60) Provisional application No. 61/256,081, filed on Oct. 29, 2009, provisional application No. 61/256,110, filed on Oct. 29, 2009.

(51) Int. Cl.
| | |
|---|---|
| *A61B 5/02* | (2006.01) |
| *A61B 5/021* | (2006.01) |
| *A61B 5/024* | (2006.01) |
| *A61B 5/0225* | (2006.01) |
| *A61B 5/022* | (2006.01) |
| *A61B 5/025* | (2006.01) |
| *A61B 5/00* | (2006.01) |

(52) U.S. Cl.
CPC ............ *A61B 5/0059* (2013.01); *A61B 5/7203* (2013.01); *A61B 5/022* (2013.01); *A61B 5/02241* (2013.01)
USPC ............ 600/485; 600/493; 600/490; 600/500

(58) Field of Classification Search
USPC .......... 600/500–504, 507, 473, 475–481, 483
See application file for complete search history.

(56) References Cited

U.S. PATENT DOCUMENTS

| | | | |
|---|---|---|---|
| 4,105,021 A | * | 8/1978 | Williams et al. ............... 600/496 |
| 4,406,289 A | | 9/1983 | Wesseling et al. |

(Continued)

FOREIGN PATENT DOCUMENTS

| | | |
|---|---|---|
| AT | 407949 | 7/2001 |
| EP | 0537383 | 4/1993 |

(Continued)

OTHER PUBLICATIONS

Peñáz J: Photoelectric Measurement of blood pressure, volume and flow in the finger. Digest of the 10th international conference on medical and biological engineering—Dresden (1973).

(Continued)

*Primary Examiner* — Navin Natnithithadha
(74) *Attorney, Agent, or Firm* — McDonnell Boehnen Hulbert & Berghoff LLP

(57) ABSTRACT

A system and method of enhancing a blood pressure signal is disclosed. The volume of an artery in a finger is measured by a photo-plesthysmographic (PPG) system, which produces a PPG signal. This PPG system is placed inside a cuff, and the cuff pressure is controlled by the PPG signal. The portion or component of the PPG signal having a frequency higher than a predefined threshold frequency is then modified or enhanced, such as by multiplying the high frequency component by a calibration factor. A blood pressure signal is then calculated using the cuff pressure and the modified PPG signal. A blood pressure contour curve may then be generated, and a variety of parameters may be calculated using the curve.

20 Claims, 9 Drawing Sheets

(56) References Cited

U.S. PATENT DOCUMENTS

| | | |
|---|---|---|
| 4,510,940 A | 4/1985 | Wesseling |
| 4,524,777 A | 6/1985 | Kisioka et al. |
| 4,539,997 A | 9/1985 | Wesseling et al. |
| 4,592,364 A | 6/1986 | Pinto |
| 4,705,047 A | 11/1987 | Bailey |
| 4,726,382 A | 2/1988 | Boehmer et al. |
| 4,869,261 A | 9/1989 | Penaz |
| 4,899,758 A | 2/1990 | Finkelstein et al. |
| 4,969,466 A * | 11/1990 | Brooks ............... 600/494 |
| 5,054,493 A | 10/1991 | Cohn et al. |
| 5,172,696 A | 12/1992 | Souma |
| 5,211,177 A | 5/1993 | Chesney et al. |
| 5,265,011 A | 11/1993 | O'Rourke |
| 5,400,793 A | 3/1995 | Wesseling |
| 5,485,838 A | 1/1996 | Ukawa et al. |
| 5,533,511 A | 7/1996 | Kaspari et al. |
| 5,535,753 A | 7/1996 | Petrucelli et al. |
| 5,575,284 A | 11/1996 | Athan et al. |
| 5,676,140 A | 10/1997 | Ukawa et al. |
| 5,746,698 A | 5/1998 | Bos et al. |
| 6,011,985 A | 1/2000 | Athan et al. |
| 6,315,735 B1 | 11/2001 | Joeken et al. |
| 6,348,038 B1 | 2/2002 | Band et al. |
| 6,394,958 B1 | 5/2002 | Bratteli et al. |
| 6,471,646 B1 | 10/2002 | Thede |
| 6,496,711 B1 | 12/2002 | Athan et al. |
| 6,616,613 B1 * | 9/2003 | Goodman ............... 600/504 |
| 6,623,434 B2 | 9/2003 | Chesney et al. |
| 6,669,648 B1 | 12/2003 | Fortin et al. |
| 6,689,069 B2 | 2/2004 | Bratteli et al. |
| 6,733,461 B2 | 5/2004 | Bratteli |
| 6,736,782 B2 | 5/2004 | Pfeiffer et al. |
| 6,758,822 B2 | 7/2004 | Romano |
| 6,932,772 B2 * | 8/2005 | Kan ............... 600/490 |
| 7,035,679 B2 | 4/2006 | Addison et al. |
| 7,144,372 B2 | 12/2006 | Ng et al. |
| 7,220,230 B2 | 5/2007 | Roteliuk et al. |
| 7,317,409 B2 | 1/2008 | Conero |
| 7,318,807 B2 | 1/2008 | Ng |
| 7,361,147 B2 | 4/2008 | Ng |
| 7,390,301 B2 | 6/2008 | Skrabal et al. |
| 7,422,562 B2 | 9/2008 | Hatib et al. |
| 7,442,169 B2 | 10/2008 | O'Rourke |
| 7,452,333 B2 | 11/2008 | Roteliuk |
| 7,503,897 B2 | 3/2009 | Ng et al. |
| 7,588,542 B2 | 9/2009 | Pfeiffer et al. |
| 7,628,758 B2 | 12/2009 | O'Rourke |
| 7,651,466 B2 | 1/2010 | Hatib et al. |
| 7,666,144 B2 | 2/2010 | Cohen et al. |
| 7,740,591 B1 | 6/2010 | Starr et al. |
| 7,803,122 B2 | 9/2010 | Pfeiffer et al. |
| 7,815,578 B2 | 10/2010 | Cohen et al. |
| 8,114,025 B2 * | 2/2012 | Fortin et al. ............... 600/485 |
| 8,343,062 B2 * | 1/2013 | Fortin et al. ............... 600/485 |
| 2005/0124904 A1 | 6/2005 | Roteliuk |
| 2005/0228298 A1 | 10/2005 | Banet et al. |
| 2006/0235323 A1 | 10/2006 | Hatib et al. |
| 2007/0032729 A1 | 2/2007 | Fortin |
| 2008/0015451 A1 | 1/2008 | Hatib et al. |
| 2008/0200785 A1 | 8/2008 | Fortin |
| 2008/0287812 A1 | 11/2008 | Parlikar et al. |
| 2009/0062666 A1 | 3/2009 | Roteliuk |
| 2009/0112113 A1 | 4/2009 | Mukkamala |
| 2009/0270739 A1 | 10/2009 | Hatib et al. |
| 2010/0016735 A1 | 1/2010 | Harpas et al. |
| 2010/0076326 A1 | 3/2010 | Cohen et al. |
| 2010/0121203 A1 | 5/2010 | O'Rourke et al. |
| 2010/0121207 A1 * | 5/2010 | Moersdorf et al. ........... 600/500 |
| 2010/0198088 A1 | 8/2010 | Ortenberg et al. |
| 2010/0204592 A1 | 8/2010 | Hatib et al. |
| 2010/0217134 A1 | 8/2010 | Van Goudoever et al. |
| 2010/0241013 A1 | 9/2010 | Hatib |

FOREIGN PATENT DOCUMENTS

| | | |
|---|---|---|
| EP | 1103217 | 5/2001 |
| WO | 96/26497 | 8/1996 |
| WO | 96/29004 | 9/1996 |
| WO | 97/15230 | 5/1997 |
| WO | 97/24982 | 7/1997 |
| WO | 99/02086 | 1/1999 |
| WO | 99/48023 | 9/1999 |
| WO | 00/72750 | 12/2000 |
| WO | 2004/075746 | 9/2004 |
| WO | 2004/086963 | 10/2004 |
| WO | 2005/037097 | 4/2005 |
| WO | 2005/055825 | 6/2005 |
| WO | 2005/084536 | 9/2005 |
| WO | 2007/062456 | 7/2007 |
| WO | 2007/134062 | 11/2007 |
| WO | 2009/101140 | 8/2009 |
| WO | 2010/091055 | 8/2010 |

OTHER PUBLICATIONS

The International Search Report with the Written Opinion for PCT/IB2010/003325.

International Search Report for Int. App. No. PCT/IB2010/003274, completed Mar. 16, 2011.

* cited by examiner

US 8,814,800 B2

APPARATUS AND METHOD FOR ENHANCING AND ANALYZING SIGNALS FROM A CONTINUOUS NON-INVASIVE BLOOD PRESSURE DEVICE

CROSS REFERENCE TO RELATED APPLICATIONS

The present application is a non-provisional of U.S. provisional patent application Ser. No. 61/256,081 filed Oct. 29, 2009, the entire contents of which are incorporated herein by reference. The present application is also a non-provisional of U.S. provisional patent application Ser. No. 61/256,110, the entire contents of which are incorporated herein by reference.

The present application is related to U.S. patent application Ser. No. 12/915,572, now U.S. Pat. No. 8,343,062, filed Oct. 29, 2010, entitled "Digital Control Method for Measuring Blood Pressure" the entire contents of which are incorporated herein by reference.

BACKGROUND

1. Field

The invention relates generally to a method of measuring blood pressure, and more particularly to a continuous non-invasive arterial pressure (CNAP) measurement where the blood pressure signal is enhanced.

2. Description of Related Art

Pulse contour analysis (PCA) is the process of calculating parameters from a blood pressure pulse, especially from the contour of the pulse wave. PCA begins with measuring blood pressure (BP).

Blood pressure may be measured in a number of ways. As one example, a standard non-invasive sphygmomanometer (NBP) may be placed on the upper arm or wrist. The NBP applies pressure to the arteries, causing them to constrict and limit blood flow. As the pressure is released, blood flow is restored in the artery, and the systolic and diastolic blood pressures may be measured. NBP measures BP intermittently and not continuously, so it cannot be used for PCA.

Another device for measuring blood pressure is a finger cuff having an infrared light source and a light detector for measuring a photo-plethysmographic (PPG) signal that is known also from pulse oximetry. This PPG-signal is fed into a control system, which produces a counter pressure in the finger cuff. It is well known that the counter pressure equals intra-arterial pressure when the PPG-signal is kept constant. Thus, the counter pressure, which is indirect equivalent to intra-arterial pressure, is measured. This method is known as "Vascular Unloading Technique," and the continuous pressure signal can be used for PCA.

Invasive devices may also be used to measure blood pressure, such as an intra-arterial catheter, for example. Intra-arterial transducers have relatively high frequency transmission (up to 200 Hz) and can therefore be used for PCA.

Some example parameters that may be calculated from the contour of the pulse wave include stroke volume (SV), cardiac output (CO), stroke volume variation (SVV), pulse pressure variation (PPV), and total peripheral resistance (TPR). In addition, PCA can be used for other measurements which give insight to the human vascular properties, for example arterial stiffness. Thus, it is desirable that the measured blood pressure signals be as accurate as possible.

Invasive devices have the disadvantage of being overly disturbing and painful to the patient, whereas signals from non-invasive devices have problems with the fidelity or accuracy of the signal.

SUMMARY

A system and method of enhancing the blood pressure signal fidelity is disclosed. In one embodiment, a method for determining a blood pressure contour curve includes placing a photo-plesthysmographic (PPG) system over an artery in a human finger, the PPG system producing a PPG signal based on volume of the artery, the PPG system including at least one light source and at least one light detector, modifying a component of the PPG signal having a frequency higher than a predefined threshold frequency, and calculating a blood pressure signal using the modified PPG signal.

In another embodiment, a computing device for determining a blood pressure contour curve is disclosed. The computing device includes a pressure cuff adapted to be placed over an artery in a human finger, the cuff including a PPG system having at least one light source and at least one light detector, a pressure sensor, and a controller for controlling the pressure in the cuff. The PPG system produces a PPG signal based on volume of the artery, and a pressure signal is calculated using the PPG signal and this pressure signal is applied to cuff and finger. The computing device modifies a component of the PPG signal having a frequency higher than a predefined threshold frequency and calculates a blood pressure signal using the cuff pressure and the modified PPG signal.

In yet another embodiment, a method for eliminating undesired signal content of a continuous non-invasive arterial blood pressure device is disclosed. The method includes placing cuff having a photo-plesthysmographic (PPG) system over an artery in a human finger, the PPG system producing a PPG signal based on volume of the artery, eliminating from the PPG signal an undesired portion of the PPG signal, and reconstructing the PPG signal from the remaining portion of the PPG signal.

BRIEF DESCRIPTION OF THE FIGURES

An exemplary embodiment of the present invention is described herein with reference to the drawings, in which.

DETAILED DESCRIPTION

A system and method of measuring and enhancing blood pressure (BP) signals is described. These modified, more accurate signals may then be used to more accurately calculate a variety of parameters for a patient, such as stroke volume (SV), cardiac output (CO), total peripheral resistance (TPR), and arterial stiffness, for example. The method extracts the AC-component of the photo-plethysmographic (PPG) signal of known "Vascular Unloading Technique" (VUT). In combination with the measured pressure signal, this signal is used as a second input for Pulse Contour Analysis (PCA).

Figure 1:
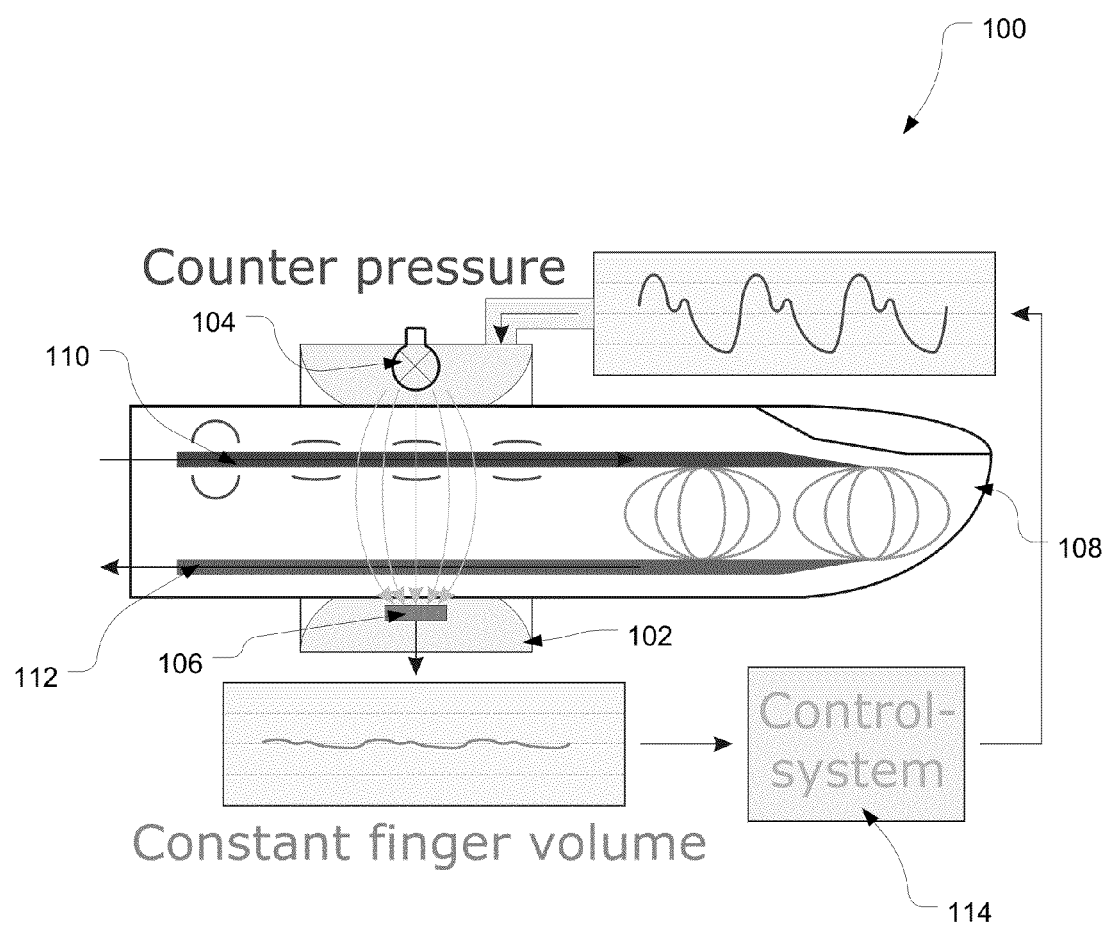
FIG. 1 shows a prior art Vascular Unloading Technique (VUT) control system using a photo-plesthysmographic (PPG) system controlling the cuff pressure for measuring blood pressure.

FIG. 1 shows a typical VUT system 100 and its control principle. The VUT system 100 is used to obtain a PPG signal, which can then be used to control the cuff pressure, which is equivalent to the continuous arterial blood pressure. The VUT system 100 includes a "photo-plethysmographic" (PPG) system located within a finger cuff 102 and having one or more light sources 104 and one or more light detectors 106. The PPG-signal is fed into a control system 114 that produces a pressure in the cuff 102.

In operation, a human finger 108 is placed in the finger cuff 102. The finger cuff 102 measures blood volume in an artery 110 of the finger 108. During systole, when blood volume increases in the finger 108, a controller 114 increases the pressure of the finger cuff 102, $p_{cuff}(t)$, until the excess blood volume is squeezed out by pressure of the cuff. On the other hand during diastole, the blood volume in the finger is decreased, and therefore the controller 114 decreases $p_{cuff}(t)$ so the overall blood volume in the artery remains constant. As blood volume and thus v(t) is held constant over time, the pressure difference between cuff pressure $p_{cuff}(t)$ and intra-arterial pressure, $p_{art}(t)$, is zero. Thus, $p_{art}(t)$ is equal to cuff pressure $p_{cuff}(t)$, which can easily be measured by means of a manometer (pressure measuring instrument), for example. Thus, intra-arterial pressure $p_{art}(t)$ itself is measured indirectly, and a PPG-signal v(t), which reflects the arterial blood volume changes in the measuring area (e.g. the finger) is obtained. As the PPG signal is kept constant, the counter pressure eliminates the arterial blood volume changes and the diameter of the artery is also constant. Thus, arterial influx is guaranteed during measurement, whereas venous return from the fingertip is slightly reduced.

This indirect measurement may not be accurate for a number of reasons. For example, v(t) is not truly constant since the pressure in the cuff may not instantly track the pressure in the artery. Thus, as the cuff pressure tracks the pressure in the artery, v(t) takes on an alternating current (AC)-like component (referred to as $v_{AC}(t)$). VUT methods rely on their valve systems as they are producing the pressure signal. Typically these valves systems are limited to upper cut-of frequencies of 15-40 Hz. Thus, the counter pressure in the cuff $p_{cuff}(t)$ is often slower than the signal origin, which produces $v_{AC}(t)$. Additional factors like pressure coupling from cuff to tissue, air supply from pump to valve system and from valve system to cuff etc. limit the control system. These factors limit VUT and lead to remaining $v_{AC}(t)$.

Additionally, pulse pressure depends on the control loop gain(s) that are either calculated from the maximum PPG signal amplitude $v_{max}(t)$ according to the "PhysioCal" criteria or chosen empirically. These gains cannot be infinity, which would be necessary for zero $v_{AC}(t)$. When calculated from $v_{max}(t)$, the controller gain could be suboptimal.

Figure 2:
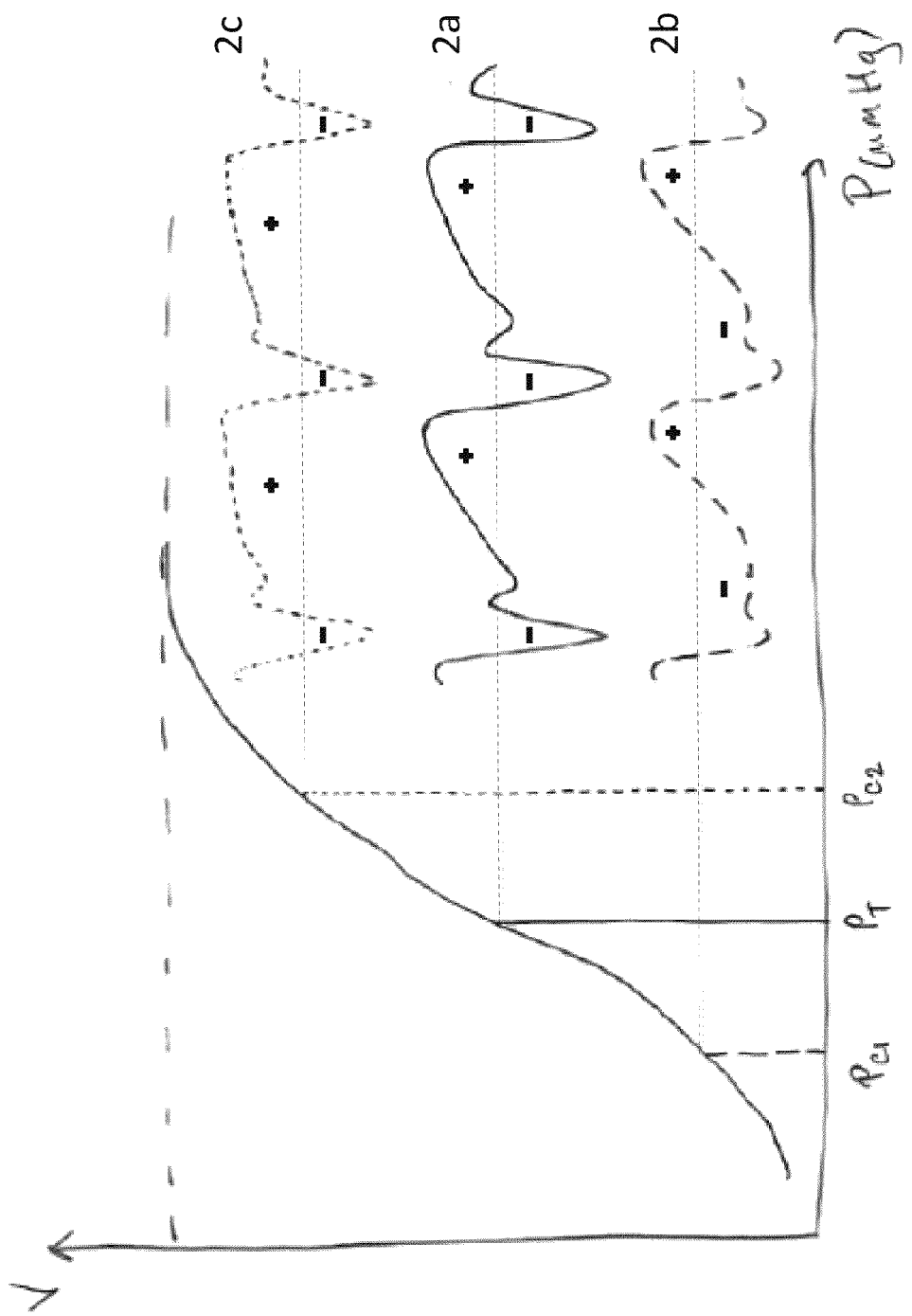
FIG. 2 describes the transfer function between PPG-signal v(t) at different constant cuff pressures.

The underlying mechanism between $p_{cuff}(t)$, $p_{art}(t)$ and $v_{AC}(t)$ is shown in FIG. 2 for constant cuff pressures ($p_{C1}$, $p_T$, $p_{C2}$) (lines 2b, 2a, 2c, respectively). A typical S-shaped p-v transmission curve produces different PPG-signals v(t) depending on $p_{cuff}$. It is well known that the amplitude of $v_{AC}(t)$ depends on $p_{cuff}$ and is highest at $p_{cuff}$=mean BP. There are different shapes of v(t) at different $p_{cuff}$.

Note the inverted characteristic of the PPG signal. The light from light source 104 is absorbed by blood. The more blood that is inside the finger (e.g. during systole), the less light is shone through the finger and detected by the light detector 106.

True mean BP is calculated as follows (for analog signals and time series):

$$\text{meanBP} = \frac{1}{T} \cdot \int_{t=0}^{T} p_{art}(t) dt = \frac{1}{N} \cdot \sum_{i=0}^{N-1} p_i \quad (1)$$

where T is the pulse interval [sec] and N is the number of samples $p_i$ of the beat.

A constant $p_{cuff}$ is used in search modes of the VUT device for detecting mean BP before the actual measurement starts. $p_{cuff}$, where PPG amplitude $v_{AC}(t)$ is at maximum, represents mean BP. This starting $p_{cuff}$ is the so called starting setpoint $p_{T0}$.

During measuring mode the loop of the control system is closed, which means that $p_{cuff}$ is alternating with respect to v(t) and depending on controller gain g. According to the VUT-principle, the amplitude of $v_{AC}(t)$ is decreasing to a minimum Ideally $v_{AC}(t)$ is zero, but this is not possible since the gain is a real value and not infinity, and the valve cut-off frequency.

Figure 3:
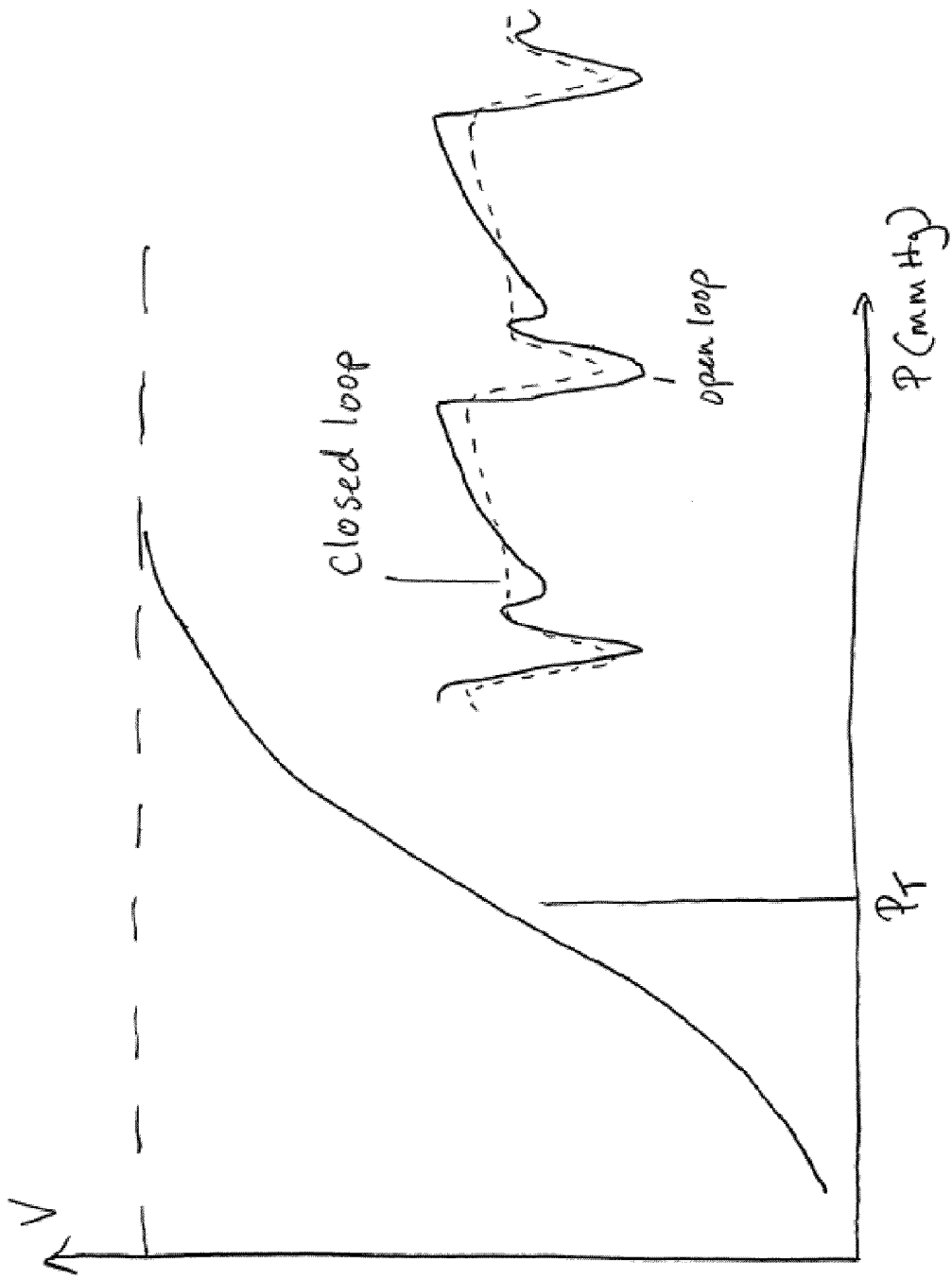
FIG. 3 shows an example pulse of the remaining PPG-signal v(t) in search (open loop) and measuring (closed loop) mode.

FIG. 3 shows the mechanism $p_{cuff}$ that is alternating around setpoint $p_T$ and is controlled by v(t). The control condition is to keep v(t), and therefore blood volume in the finger, constant. This can only be done to a minimum amplitude of $v_{AC}(t)$. Note the inverted characteristic of the control system. An increase of v(t) lowers $p_{cuff}$ and a decrease of v(t) increases $p_{cuff}$ due to the inverted characteristic of the PPG signal.

Figure 4:
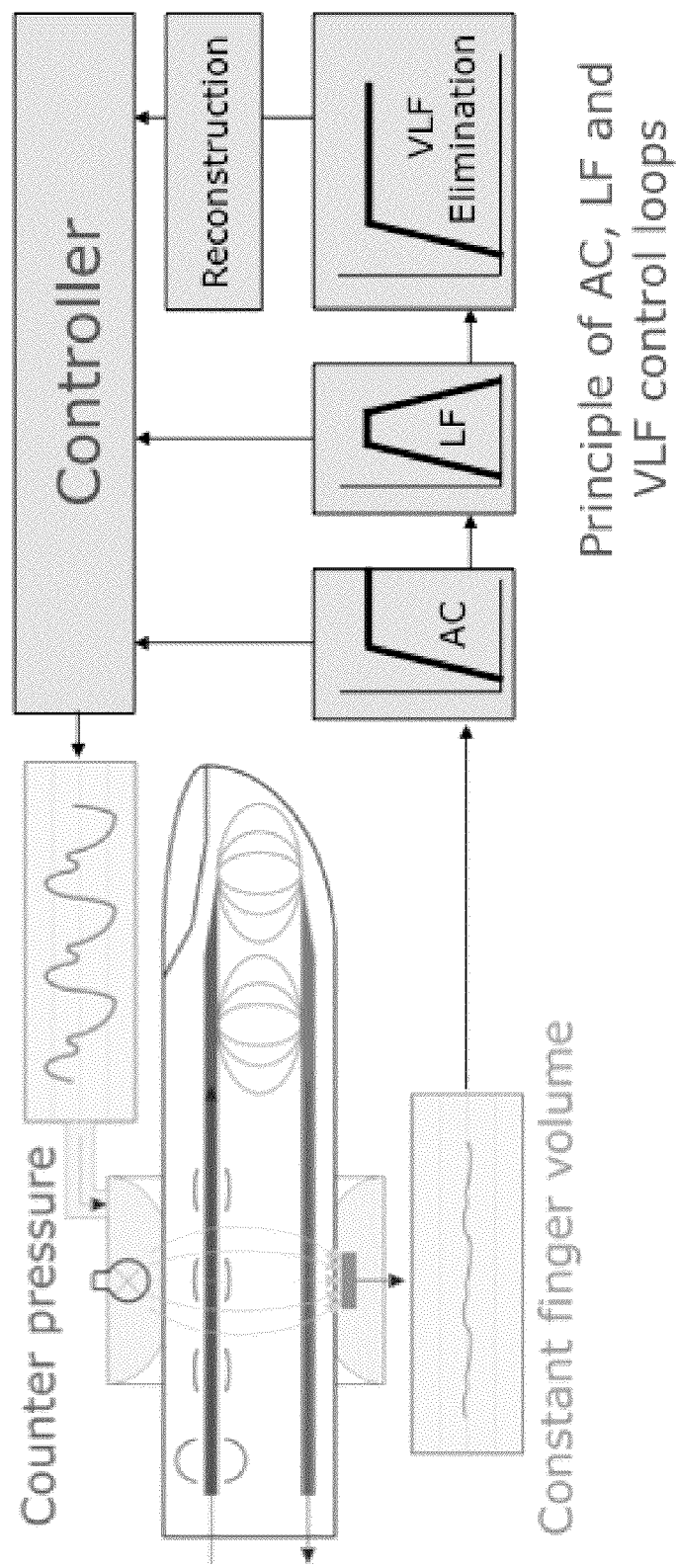
FIG. 4 shows a block diagram using different frequency ranges with different control gains and concepts.

In some embodiments, it may be advantageous to have more than one control loop. FIG. 4 shows a block diagram of such a control system. In this typical embodiment, v(t) is split into different frequency ranges. Pulsatile $v_{AC}(t)$, low frequency $v_{LF}(t)$ and very low frequency $v_{VLF}(t)$ are obtained with filters having cut-off frequencies at $f_{VLF}$ and $f_{LF}$. It is a further advantage that the three frequency ranges have different gains $g_{AC}$, $g_{LF}$ and $g_{VLF}$. This allows for optimal gain application to v(t).

The remaining pulsatile PPG signal $v_{AC}(t)$, but also other frequency bands of v(t), and the state variables of the control system (e.g. gains, cut-off frequencies, etc.) can be used for a multivariate transfer function T, which can be used for enhancing the measured $p_{cuff}(t)$ to $p_{++}(t)$. Equation (2) is a more general formula, when using n control loops:

$$p_{++}(t)=p(t)+T[v_1(t), v_2(t) \ldots v_n(t); g_1, g_2 \ldots g_n; f_{C1}; f_{C2} \ldots f_{Cn}] \quad (2)$$

It has been shown that frequency ranges below 0.1 Hz do not contribute to $p_{++}(t)$. Equation (2) for the embodiment described in FIG. 4 will be simplified as follows, because only $v_{AC}(t)$ and $v_{LF}(t)$ contribute to a meaningful signal:

$$p_{++}(t)=p(t)+T[v_{AC}(t),v_{LF}(t); g_{AC},g_{LF}; f_{LF},f_{VLF}] \quad (3)$$

A linear function can be used when the correct setpoint is applied. As can be seen in FIGS. 2-4, at the correct setpoint, $p_T$ is the point of maximal slope and therefore maximal pulsatile $v_{AC}(t)$, low frequency $v_{LF}(t)$ and very low frequency $v_{VLF}(t)$ is reached. Linear interpolation can be approximated:

$$p_{++}(t)=p(t)+T[v_{AC}(t) \cdot g_{AC}, v_{LF}(t) \cdot g_{LF}] \quad (4)$$

where T indicates the remaining transfer function after linear interpolation. In one example, T can be a vector of different scaling factors between the different linearized v(t)* gain multiples.

Due to physiological reasons, pulse wave form is different when measured at different sites (e.g. finger, upper arm, wrist, leg, etc.). Thus, because blood pressure measurement in the finger artery 110 is different from blood pressure measured at other areas of the human body, finger arterial pressure devices lack accuracy in comparison to standard devices.

One method of enhancing the VUT pressure signal $p_{cuff}(t)$, and thus increasing accuracy of the signal, is to calibrate the signal v that is measured at the finger to a standard upper arm sphygmomanometer (NBP). One reason for doing this is that there are inherent physiological and hydrostatic differences of BP measured at the finger artery as opposed to the upper arm, since the upper arm is almost close to heart level whereas the finger can be anywhere. Additionally, pulse pressure (PP) of BP depends on the control-loop gain(s) and these gains are parameters from the control system and not physiological. When the gain is determined from the maximum $v_{AC}(t)$ amplitude according to the "physiocal" criteria, this amplitude depends on the actual vascular tone (vasoconstriction or vasodilatation). This has no information about BP. When the gain(s) are chosen empirically by increasing the gain until the system start to swing with resonance frequency, these gain(s) also depends on vascular tone and system conditions. Again, this has no information about BP.

The maximum $v_{AC}(t)$ amplitude indicates only that the constant cuff pressure in search mode is equal to mean BP. The value itself is more or less a "house number" as it depends on the actual vascular tone (vasoconstriction or vasodilatation) and therefore depends on the state of the autonomic nervous system of the patient to be measured.

Calibration methods include transforming the signal along a straight line:

$$p_{++}(t)=k*p_{cuff}(t)+d \quad (5)$$

where k and d can be calculated from NBP-values as follows:

$$k = \frac{SBP - DBP}{sBP - dBP} \quad (6)$$

$$d = SBP - k \cdot sBP \quad (7)$$

where SBP and DBP are systolic and diastolic values measured from the NBP calibration device (e.g., the upper arm blood pressure cuff) and sBP and dBP are systolic and diastolic values measured from the uncalibrated finger cuff.

This method lacks accuracy because slope k is not only scaling BP-pulse, but also hypo- and hypertensive episodes. This BP-trend does not need an artificial amplification as mean BP is correctly detected by the improved VUT system. High k values overestimate BP trend, e.g., with a k=2, a drop of BP of 40 mmHg would be displayed as 80 mmHg. Even negative values could be displayed with such method. In addition, this method amplifies natural rhythms of BP, e.g., the 0.1 Hz Traube-Hering-Mayer waves, and makes them look very non-physiological.

Figure 5:
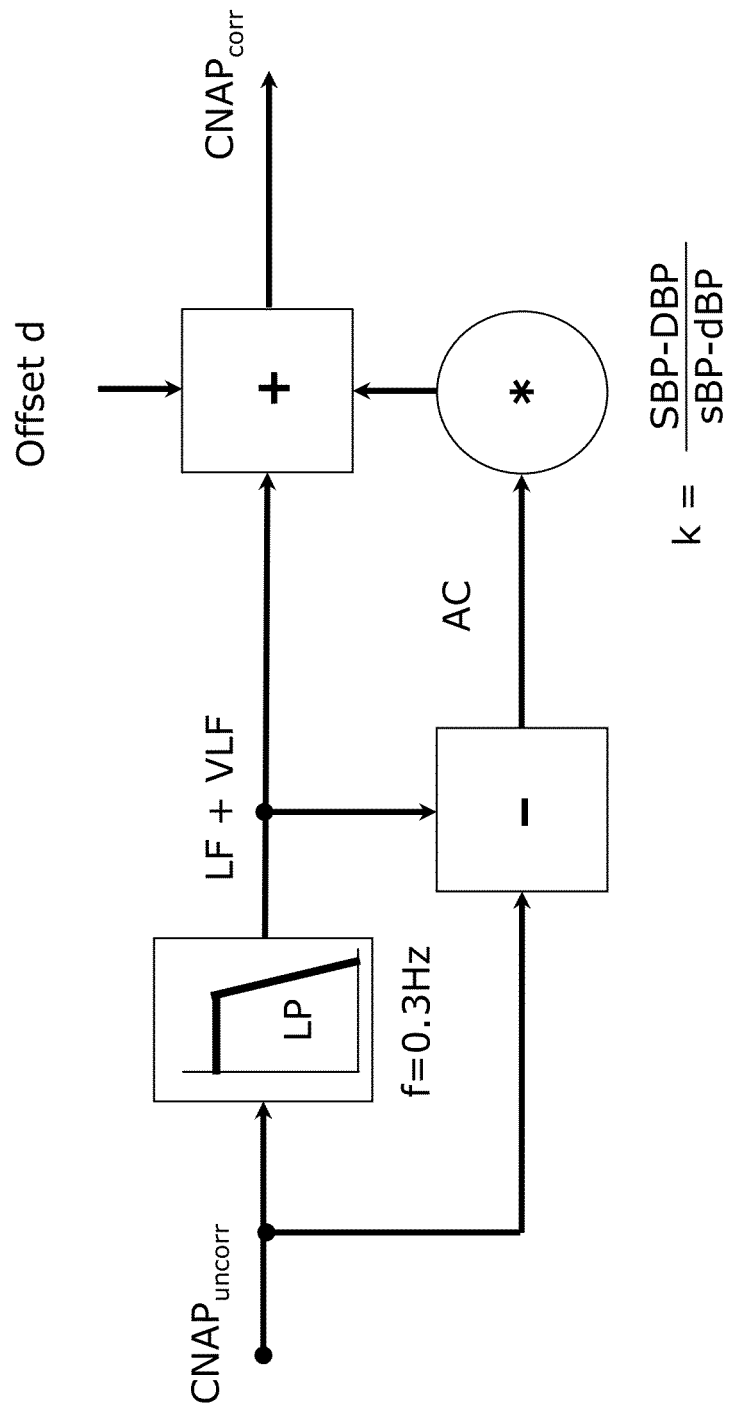
FIG. 5 is a block diagram of the calibration method.

FIG. 5 shows a method that further improves the accuracy of the signal measured by the PPG system. The method includes only multiplying the component of the signal that has a frequency content higher than some threshold value, e.g., 0.3 Hz., by slope k. Signal components lower than the cut off frequency remain unamplified. In addition, the offset d is added. Thus, the amplification formula reads as follows:

$$p_{++}(t)=k*p_{AC}(t)+p_{LF}(t)+d \quad (8)$$

where $p_{AC}(t)$ is the component of the measured pressure that has a frequency greater than the threshold frequency, and $p_{LF}(t)$ is the component of the measured pressure that has a frequency less than the threshold frequency.

Pulse wave frequency content is per se higher than the actual pulse rate or pulse frequency. For a normal pulse rate of 60 beats per minute, the pulse frequency is 1 Hz and this frequency will come down to 0.5 Hz in humans (30 beats per minute).

When a transfer function is applied in order to transfer the wave form of the pulses (e.g., from finger to upper arm wave forms) this transfer function starts with its frequency range at the lowest possible beat frequency, which is at approximately 0.3 Hz. Below that, the transfer function can be constant. It would be of further advantage if that transfer function depends on pulse frequency. This can be achieved by normalization to heart beats instead of seconds.

$$p_{brach}(t)=T_{norm}(p++(t))=p_{brach}(t)=T_{norm}(k*p_{AC}(t)+ \\ p_{LF}(t)+d)=p_{brach}(t)=p_{LF}(t)+d+T_{norm}(k*p_{AC}(t)) \quad (9)$$

As can be seen from equation (9), only the pulse frequency content $p_{AC}(t)$ has to be transform as $T_{norm}$ is constant (e.g. 1) for lower frequencies. This algorithm could be part of the PCA-method and computed within the invented device.

Another problem with known methods of detecting and enhancing VUT signals is that the underlying PPG system cannot detect changes in the blood volume due to vasoconstriction or vasodilatation (vasomotoric changes), which may be caused by drugs, for example. In other words, present systems cannot distinguish between the change of v(t) caused by vasoactivity as opposed to actual blood pressure changes. Thus, to further enhance the BP-waveform, an algorithm may used to detect changes in the blood vessel (e.g. in the finger artery) due to vasomotoric changes. The algorithm enhances the BP frequency band, where vasomotoric activities are active—in the very low frequency (VLF) band below 0.02 Hz. This VLF-band is below Traube-Hering-Mayer waves (0.1 Hz) and breathing frequency (appr. 0.2 Hz). Note that in this document both Traube-Hering-Mayer waves and breathing frequency are called LF-band as both physiological frequencies are treated within the so-called LF-loop.

Figure 6:
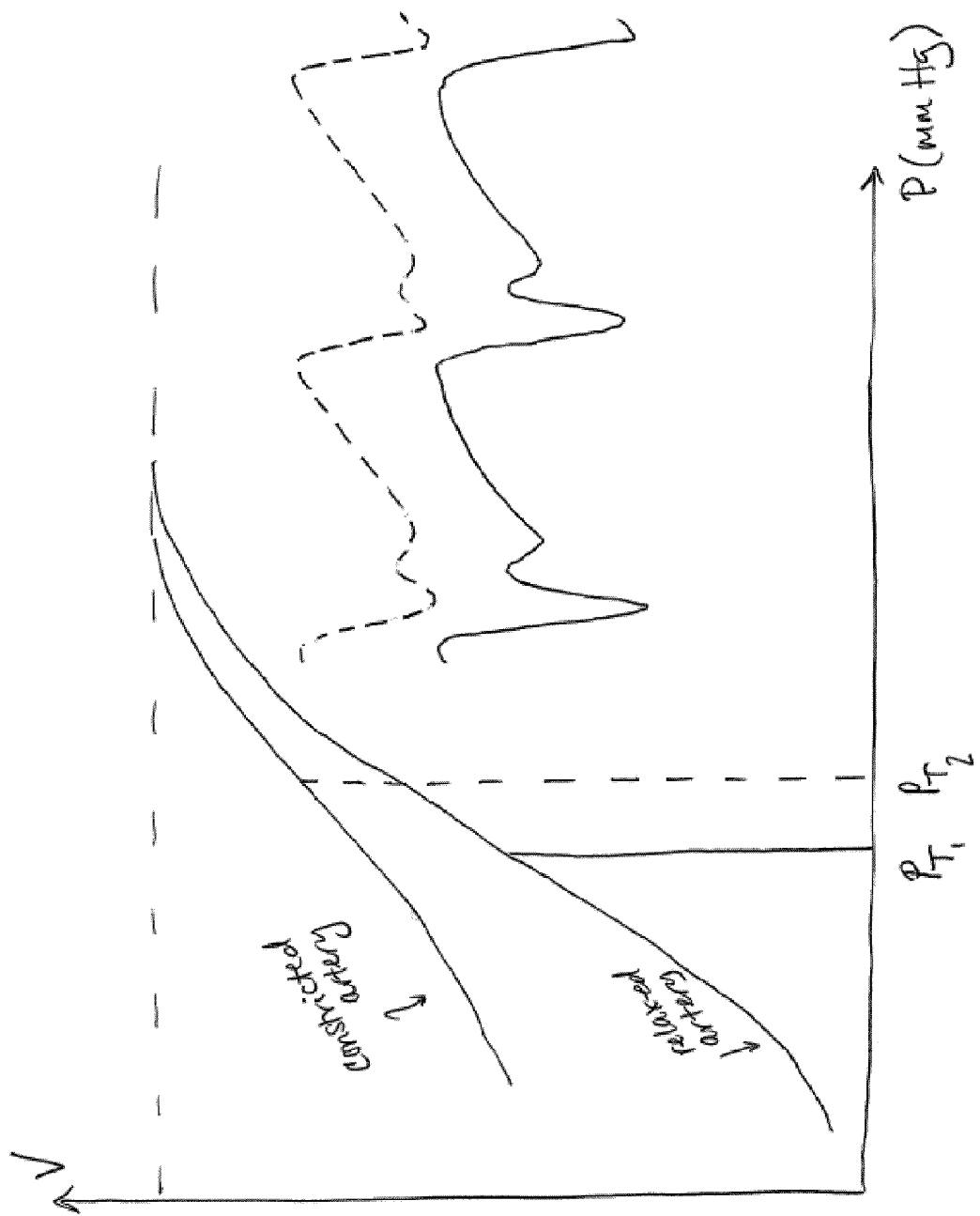
FIG. 6 shows the change in the remaining PPG-signal v(t) caused due to vasoconstriction of the artery.

The VLF-band is disturbed by vasomotoric changes coming from physiological- or drug-induced vasoconstriction or vasodilatation. FIG. 6 shows typical changes of v(t) due to vasoconstriction which is indicated with a new S-shaped transfer function. $p_{cuff}$ stays at setpoint $p_{T1}$, although setpoint $p_{T2}$ would be correct. The amplitude is decreased, but vasoconstriction produces also a more remarkable change in waveform. This behavior is used for reconstructing the VLF-band.

These vasoactivities may cause physiological BP-changes. The BP-signal is enhanced by elimination and reconstruction of VLF-band. The algorithm starts with its functionality when the control loop is closed after finding the starting setpoint $p_{T0}$ and determining at least one gain factor for at least one control loop in searching mode. $p_{T0}$ is equal to the actual mean BP.

As already described, the gain of the control system cannot be infinity and therefore $v_{AC}(t)$ is not zero. Thus, $p_{cuff}$ is not exactly equal to $p_{art}$. If $v_{AC}(t)$ is negative (systolic part), $p_{cuff}$ is following $p_{art}$ ($p_{cuff}<p_{art}$). When $v_{AC}(t)$ is in its positive (diastolic) halfwave, $p_{cuff}$ is leading $p_{art}$ ($p_{cuff}>p_{art}$).

Consider an example in which gain(s) were set to zero. In this situation, which can be seen in FIG. 2a, $p_{T0}$ and $p_{cuff}$ are at mean BP and $v_{AC}(t)$ has its maximum amplitude. The area under the negative curve equals the area under the positive half wave of the beat. Thus, $p_{art}$ is as often greater as lower in comparison to $p_{cuff}$ that indicates mean BP. This indicates that the setpoint $p_{T0}$ is correct. Therefore, this phenomenon can be used for setpoint tracking.

When the negative and the positive half wave of an alternating signal are equal the following formula is true:

$$\int_{t=0}^{T} v_{AC}(t)dt = 0 \qquad (10)$$

When this integral of $v_{AC}(t)$ over a beat is not zero, the waveform is changing. FIG. 2 describes this phenomenon: 2a shows that the positive and negative half-waves of $v_{AC}(t)$ are equal, 2b shows the signal with low setpoint and a greater negative half-wave, and 2c with high setpoint and greater positive half-wave.

Equation (10) calculates control deviation $P_n$ for the $n^{th}$ beat that indicates setpoint changes:

$$P_n = \int_{t_{n-1}}^{t} v_{AC}(t)dt \qquad (11)$$

where:
$P_n=0$->setpoint correct
$P_n<0$->setpoint to low
$P_n>0$->setpoint to high This phenomenon is also true when gain(s) are not zero, $p_{cuff}$ leads and follows $p_{art}$ and $v_{AC}(t)$ is minimized. This phenomenon is also true when the s-shaped p-v transfer function is changed due to vasomotoric changes.

Proportional control deviation P is now used for reconstruction of the VLF-band. For that, it needs also an integral part I and the new setpoint for the $n^{th}$ beat is as follows:

$$p_{Tn} = p_{T0} + g_I \cdot \sum_{0}^{n} P_n + g_P \cdot P_n \qquad (12)$$

Control loop gains $g_I$ and $g_P$ are determined in accordance with the gain $g_{AC}$ for the pulsatile part and in accordance to physiological rhythms.

This tracking (or reconstruction) algorithm allows for the elimination of the VLF-band with a high pass filter (e.g. digital filter). All frequencies content below 0.02 Hz (for example) are eliminated—only the LF-band and the pulsatile AC-component is used. Note that $v_{AC}(t)$ is calculated by subtracting $v_{VLF}(t)$ from the measured PPG signal v(t) and not by subtracting the DC-component of the signal $v_{DC}$.

Figure 7:
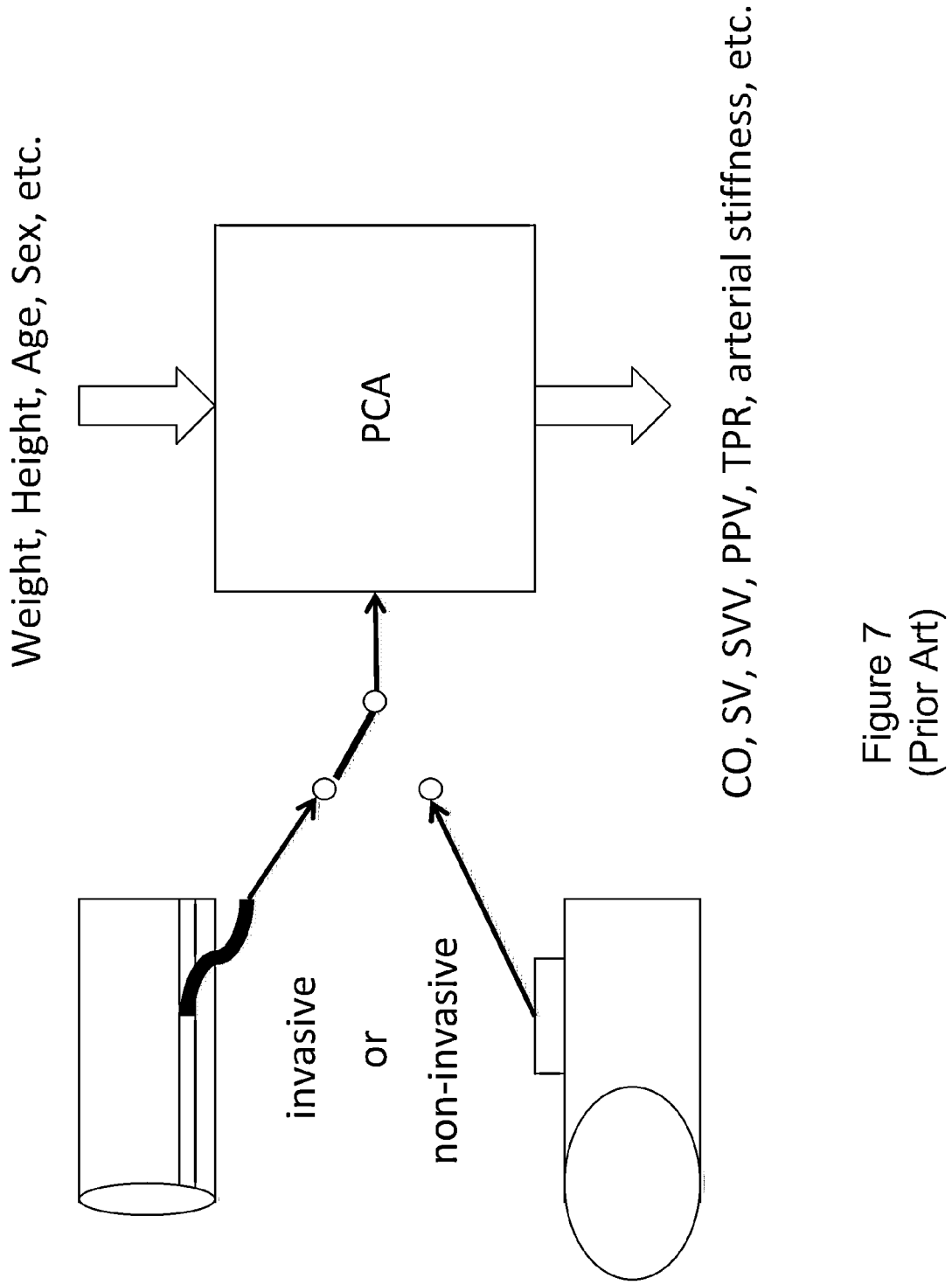
FIG. 7 describes prior art Pulse Contour Analysis (PCA) having one time varying input signal and several input parameters.

FIG. 7 shows a prior art PCA having one single time varying input signal, either an intra-arterial catheter or a non-invasive device, and several input parameters. When using VUT for PCA, $p_{cuff}$ is not equal to $p_{art}$. This is indicated by the remaining PPG-signal $v_{AC}(t)$. In addition, state variables of the control system indicate vasomotoric changes. The remaining information may also be used to enhance PCA-algorithms.

Standard PCA methods cannot be used as they must be extended with additional input signal(s) like $v_{AC}(t)$ but also signals for determining setpoint $p_T$ (which is equal to mean BP). A meaningful signal could be $P_n$ that indicates if the setpoint must be corrected due to vasomotoric changes. Further state variables can be used for determining vascular properties.

Figure 8:
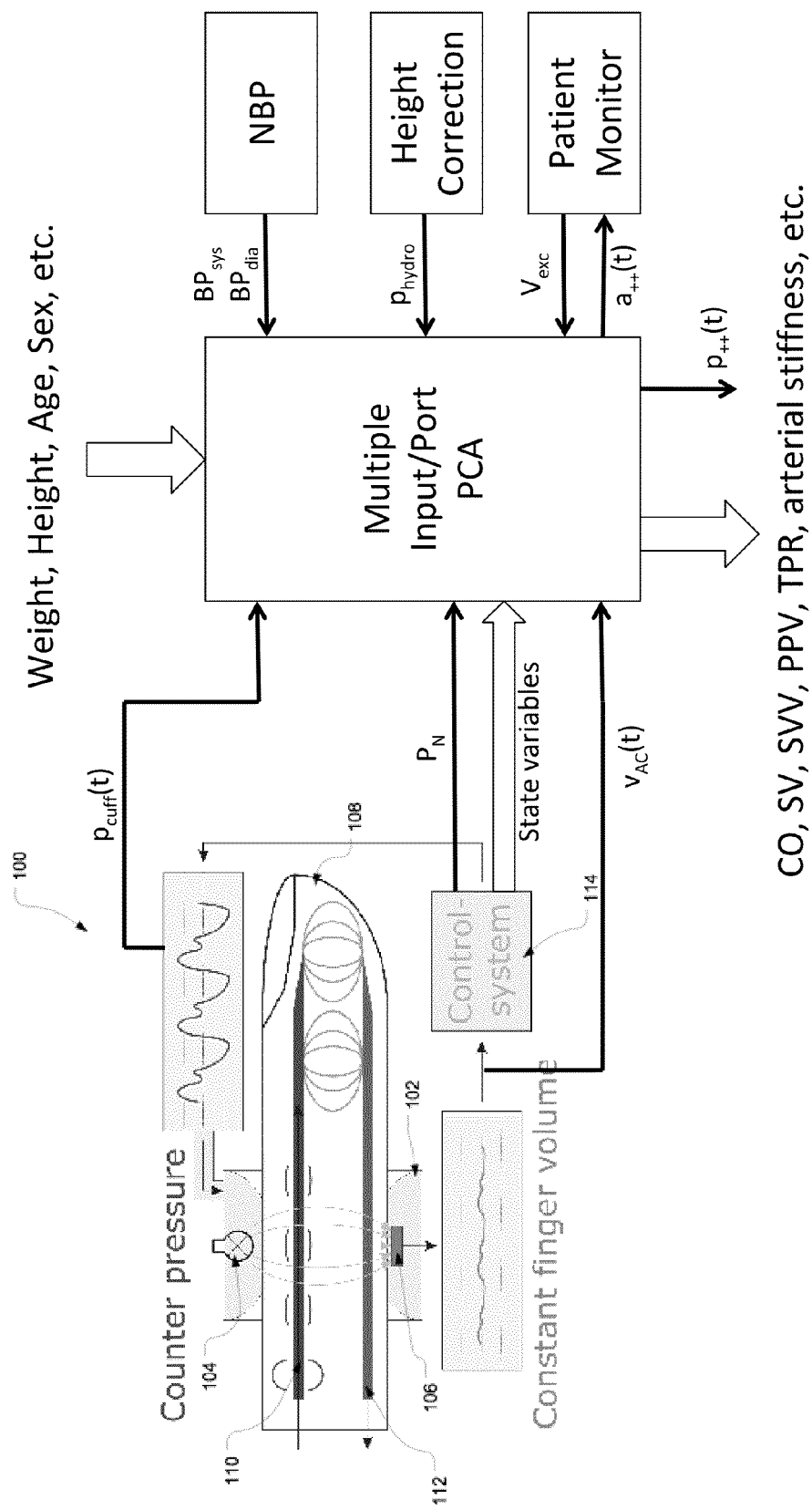
FIG. 8 is a block diagram of the new PCA-method and device.

FIG. 8 represents the block diagram of the PCA-method and device. The VUT-part provides pressure $p_{cuff}(t)$, $v_{AC}(t)$ and $P_n$ as well as state variables.

The method can also include the method for calculating the enhanced pressure signal $p_{++}$. Further, the method calculates PCA parameters like CO, SV, SVV, PPV, arterial stiffness, etc and provides and displays these parameters and $p_{++}$. In addition, the method can obtain intermittent BP-readings (like systolic BP, mean BP and diastolic BP) from a standard NBP. Further, the method can be provided with an excitation voltage from another device having an IBP-input in order to know the scaling factor of such device.

The PCA method is now a multiport network or algorithm due to multiple input signals in comparison to prior PCA with only one pressure or PPG input.

The PCA method handles these multiple inputs. One embodiment of the method is sequential mode, where $p_{++}$ is calculated first and then used for standard PCA. With that method information regarding vasomotoric changes may be lost. Thus, the preferred embodiment uses linear and non-linear multiport algorithms. In addition, these algorithms can compute signal markers from the input time series, which can be for example, areas under curves or part of the curves, duty cycles of the signals, ratios (e.g. (mean BP–dia BP)/(sys BP–dia BP)), diastolic decay, linear regressions of the signals and of the logarithmic signal statistical moments, etc. These markers can be used for the computation of PCA-parameters along with anthropometric patient information (like height, weight, age, sex, etc.) and information obtained by the VUT-control system and its state variables. The computation can be made out of multivariate polynomial equations. The weights of such multivariate equations can be either determined from physiological a-priori information or be trained with machine learning methods using a training set.

A height correcting system may also be used in conjunction with the method for enhancing the blood pressure signal. Such a height correcting system may include a fluid-filled tube where the density of the fluid corresponds to the density of blood. One end of the tube is placed at heart level and the other end is placed on the finger cuff. A free-floating membrane, which prevents the fluid from escaping, could be attached at the heart end of the tube. A pressure sensor at the finger end and connected directly to the fluid measures the hydrostatic pressure difference. The pressure sensor of the height correcting system can be constructed so that a frequency or digital signal at the sensor site is produced and submitted to the overall control system.

Providing the enhanced or modified signals described above to other devices, e.g. commercially available patient monitors, would be desirable, as all of them have an input for the standard IBP pressure. Thus, the non-invasive signal can be displayed on a screen and can be distributed to other monitoring devices. Most patient monitors have an interface for a pressure transducer in order to measure intra-arterial blood pressure (IBP). The IBP interface provides excitation voltage that is used for scaling the blood pressure signal to voltage. The enhanced signal may also be digitally distributed to further devices or computers, such as that described with respect to FIG. 9. The same applies for all calculated values like SV, CO, SVV, PPV, TPR, arterial stiffness, etc. as well as for the enhanced systolic, diastolic and mean BP values.

In order to determine the scaling range and factor, the patient monitor provides an excitation voltage. Minimum and maximum pressures are known from the specification. The excitation voltage can act as an input into the present method and can transform $p_{++}(t)$ or $p_{brach}(t)$ to a voltage $a_{++}(t)$ that emulates the output voltage of an intra-arterial transducer. The transformed and enhanced signal is transmitted to the other device. $a_{++}(t)$ can be supplied by the analogue output of the mircoprocessor/computer of the present device, an external DAC or by using a PWM-output followed by a RC filter.

Figure 9:
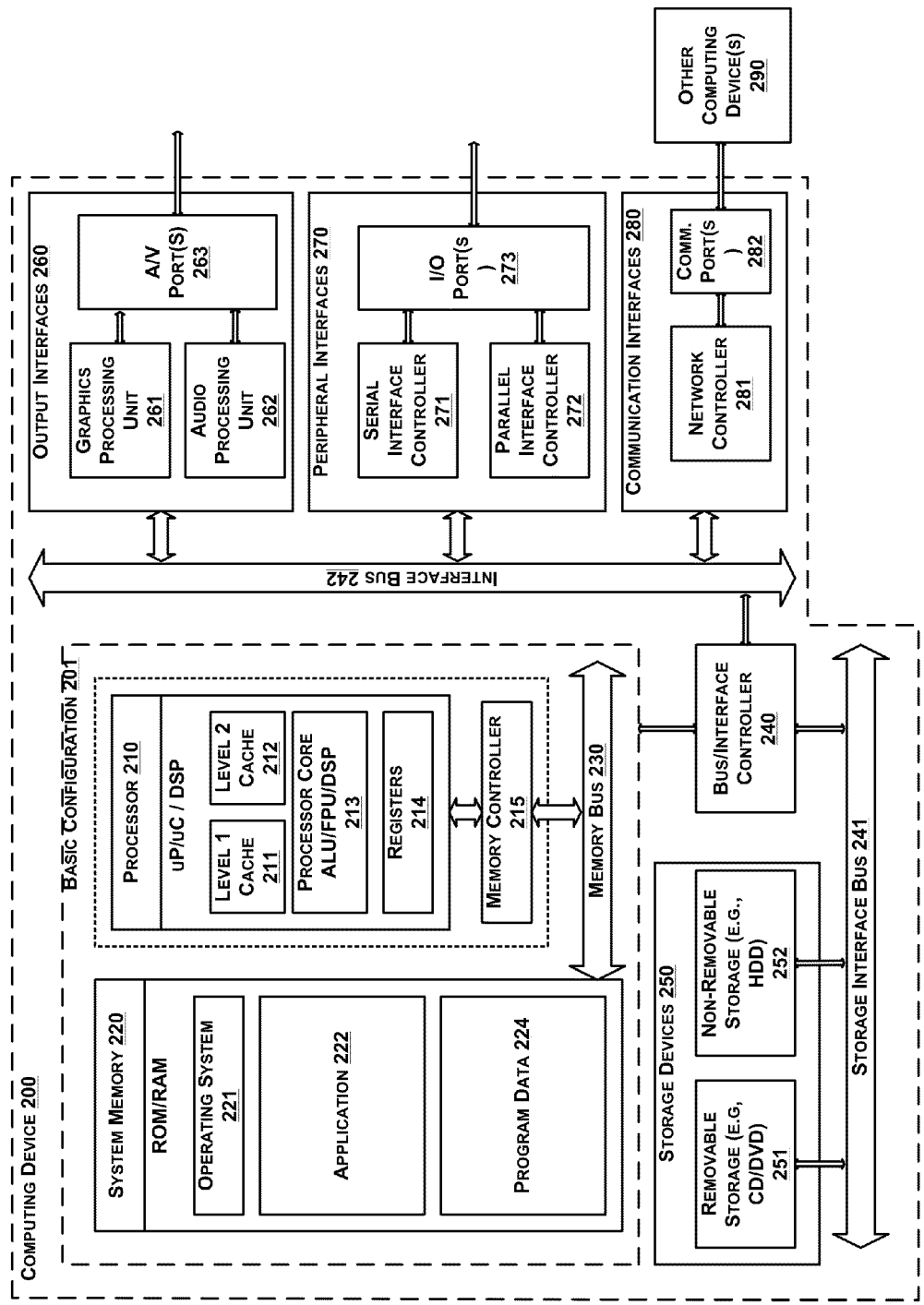
FIG. 9 shows an example computing device that may be used with the system and method of the present application.

FIG. 9 is a block diagram illustrating an example computing device 200 that may be associated with the system and method of the present application. The computing device 200 may perform the methods of the present application, including the modification of signals, calculation of values, and execution of algorithms.

In a very basic configuration 201, computing device 200 typically includes one or more processors 210 and system memory 220. A memory bus 230 can be used for communicating between the processor 210 and the system memory 220.

Depending on the desired configuration, processor 210 can be of any type including but not limited to a microprocessor (µP), a microcontroller (µC), a digital signal processor (DSP), or any combination thereof. Processor 210 can include one more levels of caching, such as a level one cache 211 and a level two cache 212, a processor core 213, and registers 214. The processor core 213 can include an arithmetic logic unit (ALU), a floating point unit (FPU), a digital signal processing core (DSP Core), or any combination thereof. A memory controller 215 can also be used with the processor 210, or in some implementations the memory controller 215 can be an internal part of the processor 210.

Depending on the desired configuration, the system memory 220 can be of any type including but not limited to volatile memory (such as RAM), non-volatile memory (such as ROM, flash memory, etc.) or any combination thereof. System memory 220 typically includes an operating system 221, one or more applications 222, and program data 224. For example, an application 222 may be designed to receive certain inputs from the PPG system and base decisions off of those inputs. For instance, the application may be designed to receive inputs from the PPG system, the NBP, and potentially other systems. As an output, the application 222 may carry out any of the methods described herein above and provide a higher fidelity BP signal.

Computing device 200 can have additional features or functionality, and additional interfaces to facilitate communications between the basic configuration 201. For example, a bus/interface controller 240 can be used to facilitate communications between the basic configuration 201 and one or more data storage devices 250 via a storage interface bus 241. The data storage devices 250 can be removable storage devices 251, non-removable storage devices 252, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage of information, such as computer readable instructions, data structures, program modules, or other data.

System memory 220, removable storage 251 and non-removable storage 252 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 200. Any such computer storage media can be part of device 200.

Computing device 200 can also include an interface bus 242 for facilitating communication from various interface devices to the basic configuration 201 via the bus/interface controller 240. Example output interfaces 260 include a graphics processing unit 261 and an audio processing unit 262, which can be configured to communicate to various external devices such as a display or speakers via one or more A/V ports 263. Example peripheral interfaces 260 include a serial interface controller 271 or a parallel interface controller 272, which can be configured to communicate with external devices such as input devices (e.g., keyboard, mouse, pen, voice input device, touch input device, etc.) or other peripheral devices (e.g., printer, scanner, etc.) via one or more I/O ports 273. An example communication interface 280 includes a network controller 281, which can be arranged to facilitate communications with one or more other computing devices 290 over a network communication via one or more communication ports 282. The communication connection is one example of a communication media. Communication media may typically be embodied by computer readable instructions, data structures, program modules, or other data in a modulated data signal, such as a carrier wave or other transport mechanism, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media. The term computer readable media (or medium) as used herein can include both storage media and communication media.

Computing device 200 can be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 200 can also be implemented as a personal computer including both laptop computer and non-laptop computer configurations.

The physician is used to blood pressure values that are obtained at heart level. As the finger could be on a different hydrostatic level, the difference between finger and heart level could be corrected with a water filled tube between these two sites. Thus, a height correcting system may be applied in order to eliminate hydrostatic difference of the finger sensor and heart level.

While the invention has been described herein with relation to certain embodiments and applications, those with skill in the art will recognize changes, modifications, alterations, and the like which still come within the spirit of the inventive concept, and such are intended to be within the scope of the invention as expressed in the following claims.

The invention claimed is:

1. A method for determining a blood pressure contour curve comprising:
    placing a cuff having a photo-plethysmographic (PPG) system over an artery in a human finger, the PPG system producing a PPG signal based on volume of the artery, the PPG system including at least one light source and at least one light detector;
    modifying, by a computing device, a component of the PPG signal having a frequency higher than a predefined threshold frequency by eliminating from the PPG signal an undesired portion of the PPG signal and reconstructing the PPG signal from the remaining portion of the PPG signal;

the cuff pressure being controlled by one or more components of the modified PPG signal; and calculating, by the computing device, a blood pressure signal using at least the modified component of the PPG signal.

2. The method of claim 1 wherein a new blood pressure is calculated using the cuff pressure and the modified PPG signal.

3. The method of claim 2 wherein modifying a component of the PPG signal having a frequency higher than a predefined threshold frequency further comprises:

separating the PPG signal into a first component having a frequency higher than the predefined threshold frequency and a second component having a frequency lower than the predefined threshold frequency;

modifying the first component; and adding the modified first component to the second component to create a modified PPG signal;

using the modified PPG signal and the cuff pressure to calculate the blood pressure signal.

4. The method of claim 2 wherein the modification further includes calibrating a component of the blood pressure signal having a frequency higher than a predefined threshold frequency using a value obtained for blood pressure by a sphygmomanometer placed on an artery in a human upper arm.

5. The method of claim 2 wherein the modification further includes multiplying a component of the blood pressure signal having a frequency higher than a predefined threshold frequency by a calibration factor, the calibration factor being calculated from a blood pressure measurement from a sphygmomanometer placed on an artery in a human upper arm.

6. The method according to claim 2, wherein the threshold frequency is about 0.3 Hz.

7. The method according to claim 2, wherein the calculation uses anthropometric parameters.

8. The method according to claim 2, further comprising calculating physiological parameters from the blood pressure contour curve.

9. The method according to claim 8, wherein the parameters are calculated by using multiport algorithms.

10. The method according to claim 8, wherein the parameters are calculated by using one or more markers of input signals.

11. The method according to claim 1, wherein the reconstruction is calculated from the pulsatile part of the remaining portion of the PPG signal.

12. The method according to claim 11, wherein the reconstructed PPG signal is $$p_{Tn} = p_{T0} + g_I \cdot \sum_0^n P_n + g_P \cdot P_n \text{ and } P_n = \int_{t_{n-1}}^{t} v_{AC}(t) dt.$$

13. The method according to claim 1, wherein the part of the PPG signal having the undesired portion of the PPG signal is below a predetermined frequency.

14. A device for determining a blood pressure contour curve comprising:

a pressure cuff adapted to be placed over an artery in a human finger, the cuff including a PPG system having at least one light source and at least one light detector;

a pressure sensor;

a controller for controlling the pressure in the cuff;

wherein the PPG system produces a PPG signal based on volume of the artery, a pressure signal is calculated by a computing device using the PPG signal, and the pressure signal is continuously applied to the cuff and finger;

wherein the computing device modifies a component of the PPG signal having a frequency higher than a predefined threshold frequency and calculates a blood pressure signal using the cuff pressure and the modified PPG signal; and wherein the controller uses the one or more components of the modified PPG signal to control the pressure in the cuff.

15. The device according to claim 14, wherein the computing device receives control state information from the controller.

16. The device according to claim 14, wherein the computing device receives information from a calibration device.

17. The device according to claim 14, wherein the computing device receives scaling information from another device.

18. The device according to claim 14, where the computing device receives information from a hydrostatic correction system.

19. The device according to claim 12, wherein the computing device receives anthropometric information from the patient.

20. The device according to claim 14, wherein the computing device calculates physiological parameters from one or more input signals.

* * * * *